(12) United States Patent
Zoth et al.

(10) Patent No.: US 7,976,474 B2
(45) Date of Patent: Jul. 12, 2011

(54) EAR CANAL OBSTRUCTION DETECTING ACOUSTICAL STIMULATION EAR PROBE

(75) Inventors: Peter Zoth, Gilching (DE); Andre Lodwig, Worthsee (DE); Johann Oswald, Grafing (DE); Thomas Janssen, Tuntenhausen (DE)

(73) Assignee: PATH medical GmbH, Germering (DE)

( * ) Notice: Subject to any disclaimer, the term of this patent is extended or adjusted under 35 U.S.C. 154(b) by 68 days.

(21) Appl. No.: 12/321,707

(22) Filed: Jan. 23, 2009

(65) Prior Publication Data
US 2010/0191144 A1 Jul. 29, 2010

(51) Int. Cl.
*A61B 5/00* (2006.01)
*A61B 5/103* (2006.01)
*A61B 5/117* (2006.01)

(52) U.S. Cl. ......... 600/559; 600/560; 600/561; 600/587

(58) Field of Classification Search .......... 600/559–561, 600/587, 25; 381/23.1, 312, 60; 181/129; 73/585, 645; 623/24; 607/46
See application file for complete search history.

(56) References Cited

U.S. PATENT DOCUMENTS

| 4,688,582 | A * | 8/1987 | Heller et al. | 600/559 |
| 6,110,126 | A * | 8/2000 | Zoth et al. | 600/559 |
| 6,231,521 | B1 * | 5/2001 | Zoth et al. | 600/559 |
| 6,331,164 | B1 * | 12/2001 | Shaw et al. | 600/559 |
| 6,786,873 | B2 * | 9/2004 | Zoth et al. | 600/559 |
| 7,050,592 | B1 * | 5/2006 | Iseberg et al. | 381/60 |
| 7,223,245 | B2 * | 5/2007 | Zoth et al. | 600/559 |
| 7,258,671 | B2 * | 8/2007 | Wasden | 600/559 |
| 7,269,262 | B2 * | 9/2007 | Iseberg et al. | 381/60 |
| 2003/0065252 | A1 * | 4/2003 | Zoth et al. | 600/300 |
| 2003/0144603 | A1 * | 7/2003 | Zoth et al. | 600/559 |
| 2004/0171965 | A1 * | 9/2004 | Zoth et al. | 600/559 |
| 2007/0156063 | A1 * | 7/2007 | Zoth et al. | 600/559 |
| 2010/0191144 | A1 * | 7/2010 | Zoth et al. | 600/559 |

* cited by examiner

*Primary Examiner* — Jeffrey G Hoekstra
(74) *Attorney, Agent, or Firm* — Marcus G. Theodore

(57) ABSTRACT

An illuminated acoustical stimulation ear probe with outer ear illumination and a probe-fit status indicator.

19 Claims, 4 Drawing Sheets

EAR CANAL OBSTRUCTION DETECTING ACOUSTICAL STIMULATION EAR PROBE

BACKGROUND OF THE INVENTION

1. Field

This invention relates to acoustical stimulation ear probes. In particular, it relates to an ear canal status and ear canal obstruction detecting acoustical stimulation ear probe with outer ear illumination and a probe-fit status indicator.

2. State of the Art

For several audiological methods, a defined sound stimulation of the ear is desired. Moreover, to record otoacoustic emissions, a microphone is to be coupled to the ear canal. The standard way to achieve this is a so-called ear probe, containing at least one speaker and one microphone coupled to the ear via so-called ear tips.

To guarantee a defined stimulation over the complete desired frequency range, and to be able to record otoacoustic emissions, good probe placement is needed. Good in this context means that there should be a good seal between probe and ear canal, no earwax or other debris occludes the ear canal or the probe, and that the probe sits comfortably in the ear canal. This often includes the task of picking the optimal ear tip from a range of available sizes to insure the required sealing.

Audiological tests are often performed in a rather dark environment, such as sound booths or bassinets in the case of newborn hearing screening. The poor visibility makes it hard to achieve good probe placement with the criteria named above. Some examiners already make use of torches (flashlights) to overcome the issue, but these tie up a hand often needed for probe positioning.

For the visual inspection of the outer ear, so-called otoscopes exist. These usually contain a light source to illuminate the ear canal and the ear drum. These devices, however, do not contain any electro acoustical components to stimulate the ear or to record sound from the ear canal.

There thus remains a need for an emitter using different light, sound, and other frequencies to identify obstructions in the inner ear channel associated with an acoustical stimulation ear probe to aid in positioning and sealing the probe. The device described below provides a probe with integrated source emitting visual or not visual frequencies, or sounds, which allows better probe placement without the need of any additional light. This makes:

- probe placement easier, as no additional light source has to be operated
- less interference with sleeping subjects, such as very young children, so they don't awake because of additional light that would otherwise be used
- improved test performance on average through better probe placement with calmer subjects

SUMMARY OF THE INVENTION

The invention comprises an ear canal obstruction detecting acoustical stimulation ear probe. It has an illuminated or variable frequency emitter associated with an ear canal probe with an acoustical stimulator sized with structure to fit within and seal to the ear canal. Specifically, it comprises a housing with an exterior sized for hand positioning the probe. The housing has a tip structured to fit and seal within an ear canal. The housing interior defines a light transmission and inspection passageway with an opening at the tip through which light may pass and project into the inner ear for inspection. The passageway may be open or translucent, such as when an optical cable is housed within the housing interior. A translucent or partly translucent probe tip could also be an optical duct.

In one preferred embodiment the housing is tubular with a passageway connecting a tip opening at one end and the viewing portal in communication with the passageway at the other end. This allows the tester direct visual inspection of the ear canal for proper probe placement. In another preferred embodiment, a camera is mounted within the passageway to record images of the ear canal during testing.

An acoustical stimulator, such as an acoustical transducer, which sends sound signals and receives otoacoustical signals is mounted within the housing passageway with leads extending from the housing. A power source operably associated with the leads of the acoustical stimulator to activate the acoustical stimulator to send sound signals and receive otoacoustical signals. A microprocessor is associated with the acoustical stimulator to process the otoacoustical signals. A frequency emitter is associated with the housing passageway to radiate energy from the passageway into the ear canal to identify wax or other obstructions for removal before sound testing. A light source is associated with the housing passageway and powered by the power source to pass through the passageway and illuminate the outer ear while the probe is being placed.

To aid in proper placement, the ear probe may include a sensor associated with the housing tip structure, which generates an ongoing signal to the microprocessor when the housing tip structure is property seated within the outer ear channel of a test subject. An indicator is attached to the exterior of the housing and associated with the microprocessor, which activates the indicator when the sensor signal indicates the housing tip structure is properly seated within the outer ear channel of the test subject.

A typical acoustical stimulator includes at least one speaker and at least one microphone, which can be used to evoke and record otoacoustic emissions. It can also be used to provide the stimulation for other objective tests, such as auditory evoked potentials (AEP). Moreover, it can be used as a sound source for subjective audiometry, such as pure tone audiometry or speech audiometry.

In the case of transiently evoked otoacoustic emissions, TEOAE, a response to transient acoustic stimuli is recorded by the microphone. The response is typically evaluated using statistical methods, such as averaging, to separate the TEOAE from stimulus artifacts and noise.

However, the acoustical stimulator may be of more complex construction to measure the frequency product generated by the cochlea in response to the generated stimulus measured with the aid of a microphone, which generates an analogue electronic signal fed to an input amplifier. These frequencies of the mixed products of the electronic signal are analyzed with the aid of a frequency analyzer before employing a phase analyzer. The phase analyzer is generally employed to evaluate the $3^{rd}$ order intermodulation product like (2f1−f2), where f2 is approximately equal to 1.2 times f1. This provides the greatest signal amplitude for statistical evaluation.

The acoustical stimulator generally has a number of leads connected to and controlled by a microprocessor where evaluation is done automatically by means of strict signal statistical criterion. Analysis is based on the measurement and statistical analysis of otoacoustic emissions (OAE's), which are signals generated by the hair cells of a functioning inner ear in response to acoustic stimuli as a result of the non-linear properties of the cochlear amplifier.

A probe as described above can also be extended by a tube connector in order to be used for Tympanometrie.

Mounted within the housing is a light source operably associated with a power source to activate the light source to direct light through the passageway into the ear canal to aid in placement and sealing of the probe. A chemical light source could also be included in the disposable lighted tip, using Chemiluminescence as a source of light, as used in so-called light-sticks.

The light source illuminates the outer ear canal to show earwax or other debris, which occludes the ear canal and is removed during the probe placement. In another embodiment the light source is a variable color frequency emitter, which uses a different frequency to show earwax or other debris, which occludes the ear canal.

The light source preferably is an LED or other light emitter and is generally powered by the devices that power the ear probe. Alternatively, it could be an optical fiber associated with the probe tip that conducts light from an external light source through an optical duct to the probe tip. The light may be switched on manually or is automatically activated when the probe placement or calibration procedure is started. The automatically activated probe can contain an extra switch or pushbutton to allow manual switching of the illumination.

The invention thus provides a probe with integrated lamp or variable frequency emitter, which allows better probe placement without the need of any additional light.

In addition, the following features may be included:
1. An additional or the same light source serves as a indicator, which can signal test progress, probe placement quality parameters, environmental noise or other things to the user while placing the probe or while a test is running. It could also indicate the end of a test and/or its result. The user may be guided by these indications to place the probe, select the ear, clean the probe etc. Since the microprocessor has typically control over the light sources and over the stimulus and response, it can use all of this information to guide the user.
2. A magnifier lens may be mounted within the passageway of the housing to aid in ear canal inspection to the probe function. This lens could be integrated either in the probe body or in the probe tip and would allow the user to inspect the ear canal for debris or pathologic issues.
3. A camera attached to the housing to aid in ear canal inspection to the probe function A CCD or CMOS digital camera module can be integrated into the probe to provide instant imaging or photographing of the ear canal or eardrum. A graphic display in the main unit would display an instant image recorded by the probe camera to provide information of the outer ear and middle ear status (otoscopy).

Currently probe fitting is done often in a sound proof room. Newborns and children often are laid on their back or on one side. The closest light source is far from the baby's head, in order not to annoy the baby. Therefore often the insertion of the ear-probe is done under bad or moderate light conditions. Therefore the tester often cannot inspect the outer ear for occlusion or debris before the ear-probe is inserted in the ear-canal. If the outer ear canal is occluded, the emitted sound will get attenuated by the debris in the outer ear. In addition, the evoked responses from the cochlear (OAE's) are attenuated as well. This often leads to a 'REFER' result and a low specificity in the hearing screening program. Statistically it is shown, that high percentages of the 'REFER' results of OAE-measurement are due to outer-ear occlusions or debris. So, an occluded outer ear canal often will lead to a 'REFER' result.

In order to detect occlusions of the ear-canals a light source or frequency emitter is integrated into the probe illuminating the outer ear-canal during insertion of the ear-probe. The tester will therefore be able to detect an occlusion and take the necessary steps for cleaning or postponing the acoustic testing. Furthermore the tester will be able to detect other problems with the ear canal (such as anatomical structural problems where the ear-canal is strongly bowed). This allows the tester a better and exact ear-probe placement and fitting. Again, the better the ear-probe is fitted the lower the 'REFER' rate will be.

The second improvement is that the positioning and the probe seal in the outer ear canal will be continuously monitored during the measurement testing. The result of the fitting is continually monitored and is indicated with a light emitter source or LED in the probe itself. A frequency emitter placed in the ear probe continuously emits sound, light, ultrasound, laser frequency, etc. energy during gaps in the acoustical measurement. This emitted energy is partially reflected by the outer ear or the eardrum. A corresponding frequency receiver in the ear probe such as a microphone, ultrasound receiver, laser receiver, responds to the reflected energy via amplifiers and filters to prepare a signal for micro processing. The frequency emitter and the frequency receiver thus can be used at the same time for audiological measurements.

The microprocessor automatically checks the signal to determine if the ear probe fit is correct before the acoustical measurement is started. Information about the probe fit is provided instantly via a light, LED, optic lead, or other indicator. Usually the indicator is positioned directly within the ear probe or on the surface of the ear probe. The indicator signal advises the tester to check and improve the fitting without having to consult remote test instruments or screening devices, or laptops. As the status of the fit is automatically monitored during the acoustic measurement and indicated via the ear-probe as described above, the tester is free to concentrate on and to watch the baby or person tested and monitor the test results.

DESCRIPTION OF THE ILLUSTRATED EMBODIMENTS

Figure 1:
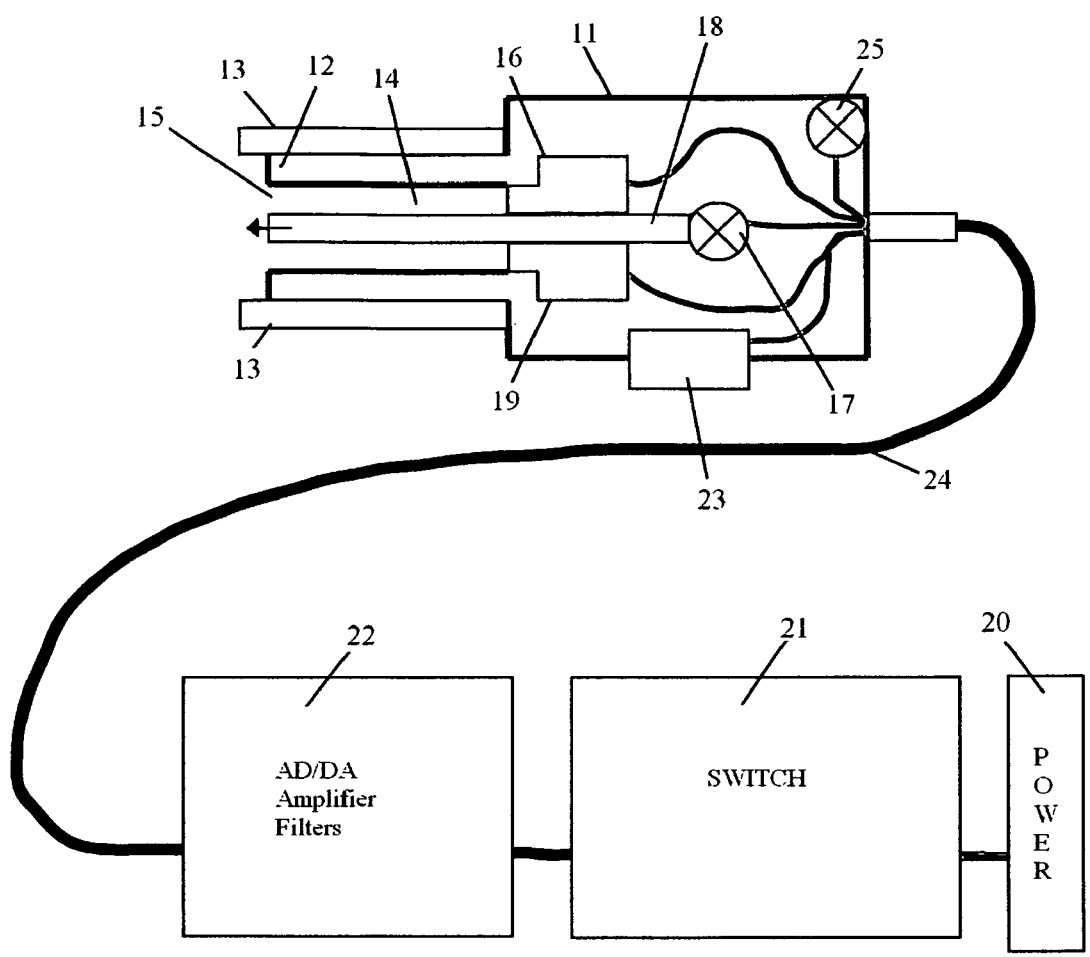
FIG. 1 is a cross-sectional view of one preferred embodiment.

FIG. 1 is a cross-sectional view of one preferred embodiment of the illuminated ear probe 10. It consists of a flexible soft housing 11 with an exterior sized for grasping and positioning of the probe 10. The housing 11 has a tip 12 constructed of a material, which will form a seal with the inner ear canal. In this embodiment, a plurality of interchangeable different sized ear tips 13 are removably mounted onto the tip 12 as required to seal different sized ear canals before testing.

The housing 11 defines an interior passageway 14 leading to an opening 15 defined by the tip 12 to view the interior of the ear canal when the probe 10 is placed.

Mounted within the housing 11 is a speaker 16 and a lamp 17 attached to an optical duct 18. Mounted opposite the speaker 16 is a microphone 19, which picks up otoacoustical signals received in response to signals generated by the speaker 16. Preferred housing 11 materials are soft plastics, rubbers, and similar materials.

These components are operatively connected to a power source 20, and a microprocessor 21, which analyzes the otoacoustical signals. AD/DA Amplifier Filters 22 may also be included. An optional switch 21 to turn the probe 10 on and off may be included as shown on the housing 11. Leads 24 connect the power source 20 to the various components.

A signal lamp 23 may be included associated with a sensor (not shown), which senses if the soft housing tip 12 or 13 has formed a seal with the ear canal by noting pressure or sound energy changes within the sealed ear canal. The sensor may be a pressure or contact sensor associated with the tip 12 or 13, which generates an ongoing signal when the tip 12 or 13 is properly sealed within the outer ear channel and sends it to the microprocessor 21. This signal lamp 25 tells an operator if an effective seal has been achieved to insure accuracy of the sound measurements.

The microprocessor 21 in one variation sends a signal to the signal lamp 25 preferably structured as a multi-colored light attached to the housing 11 that changes colors when the probe is properly seated within the outer ear channel.

In this embodiment, the housing tip 12 opening 15 transmits light within the outer ear canal to act as a flashlight before insertion. Thereafter, improper probe 10 placement is detected by erratic testing signals measured by the microprocessor 21.

Figure 2:
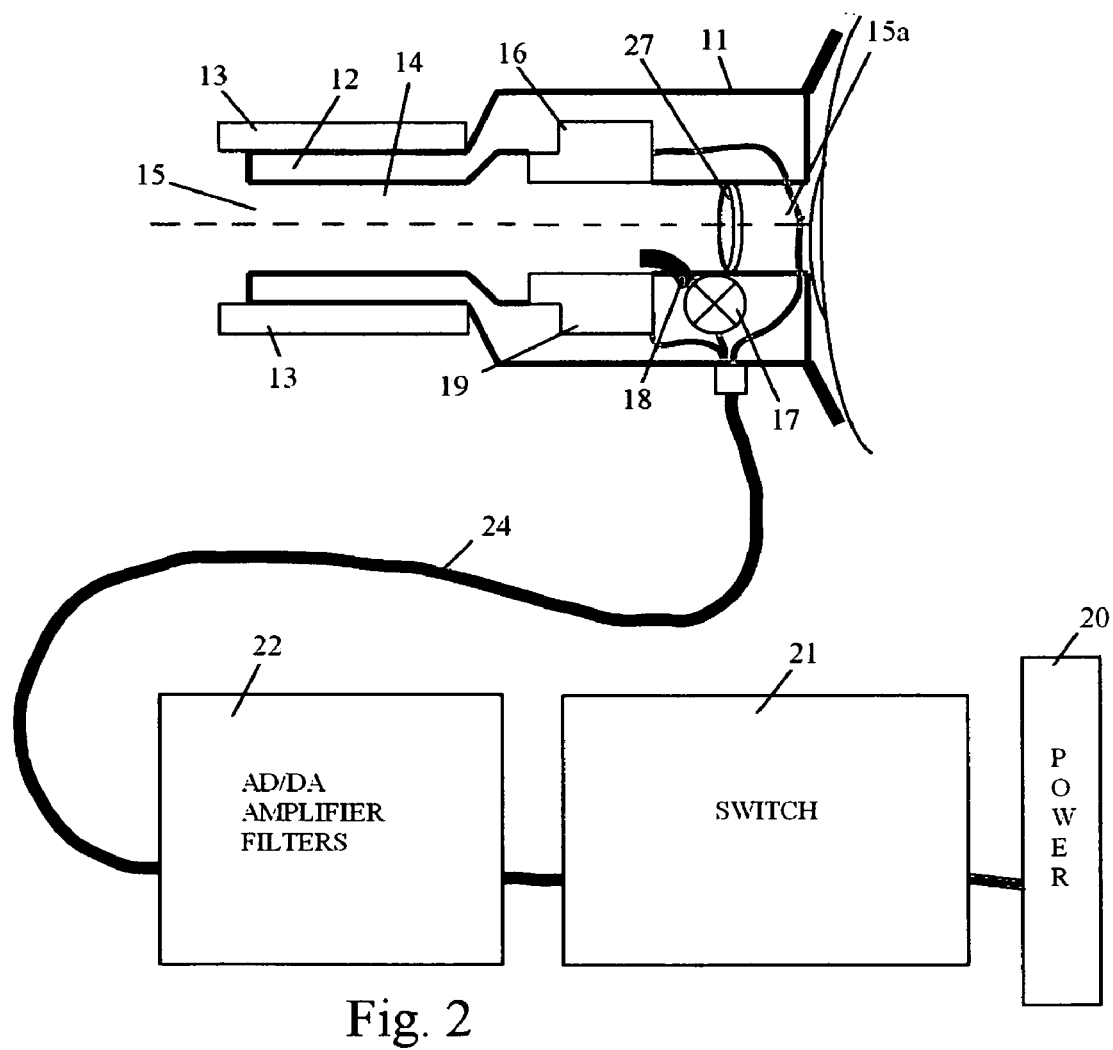
FIG. 2 is a cross-sectional view of another preferred embodiment.

FIG. 2 is a perspective view of another cross-sectional embodiment of the invention. The illuminated probe 10 has a tubular housing 11 with an exterior sized for probe 10 positioning. It has a tip end 12 adapted to received interchangeable different sized ear tips 13 to fit and seal within different sized an ear canals. The housing 11 defines an interior passageway 14 leading to an opening 15 defined by the tip end 12 to view the interior of the ear canal when the probe 10 is inserted. At the other viewing end of the housing 11, is a viewing portal 15a in communication with the passageway 14. The tubular housing 11 passageway 14 thus defines a longitudinal viewing plane with open ends 15, 15a through which a tester peers. A magnifier lens 27 may be attached to the housing 11 intercepting the viewing plane for magnified ear canal inspection.

Mounted within the tubular housing 11 passageway 14 is an acoustical stimulator speaker 16 similar to that described above, which sends sound signals and receives otoacoustical signals.

Leads 24 extend from the housing 11 to a power source 20 operably associated with an acoustical stimulator shown as a speaker 16 to activate it to send sound signals and receive otoacoustical signals via the microphone 19.

A microprocessor 21 is associated with the microphone 19 to process the otoacoustical signals.

A frequency emitter shown as a lamp 17 associated with an optical duct 18 is attached to the tubular housing 11 as shown to project light through the passageway 14 and into the ear canal to identify wax or other obstructions for removal before sound testing.

Figure 3:
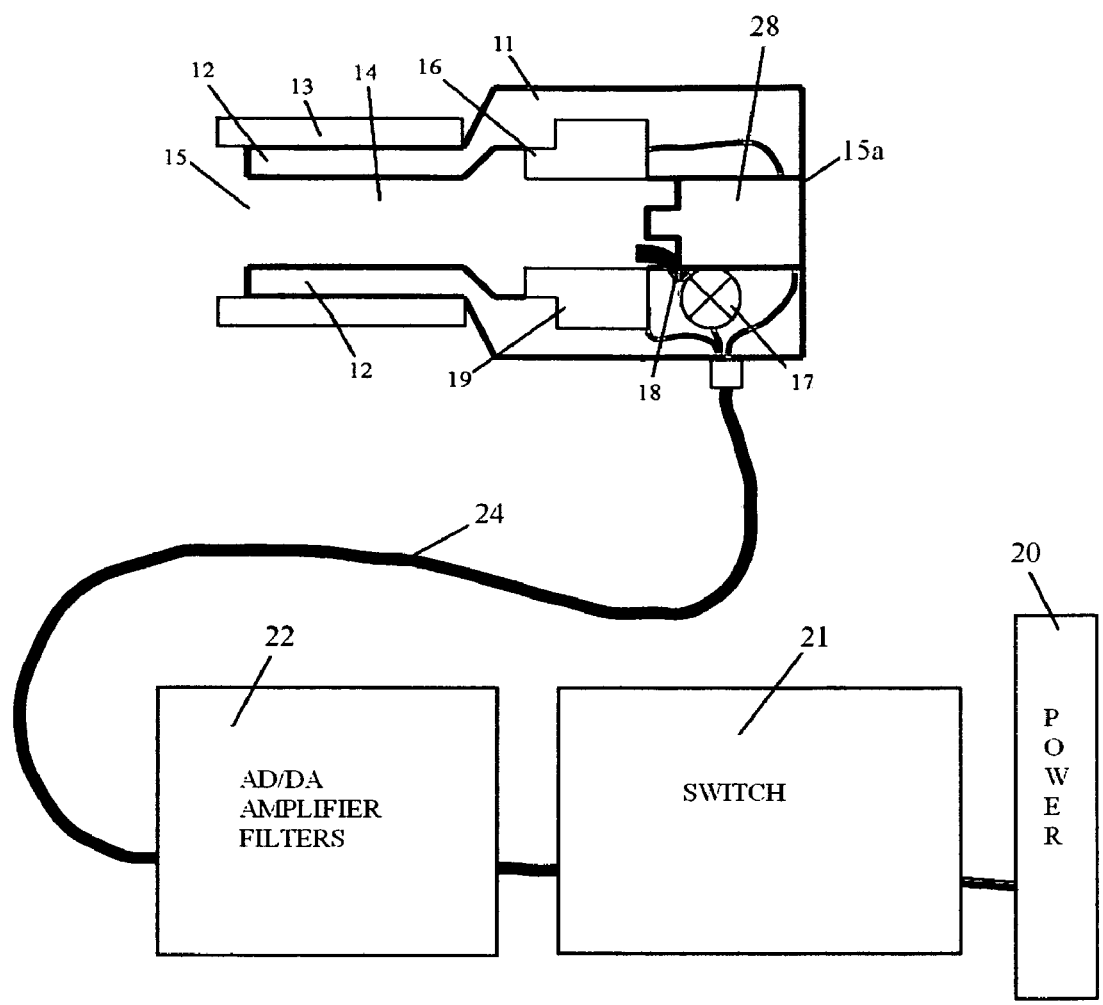
FIG. 3 is a cross-sectional view of another preferred embodiment employing a camera.

This embodiment provides the tester with a lighted view of the inside of the outer ear when the probe 10 is placed in position FIG. 3 is another variation employing a camera 28 inserted within a housing 11 at the viewing end 15a of the passageway 14. The open end 15 allows the camera 29 to record ear canal inspections during testing.

The illuminated probe 10 is used by inserting its tip 12 into the outer ear canal, turning it on to identify any wax or debris build-up, which needs removal for a proper seal, removing the same, and then positioning the probe 10 to form a seal with the outer ear canal. The sound speaker 16 is then activated and the otoacoustical signals picked by the microphone 19 and processed by the microprocessor 21.

Figure 4:
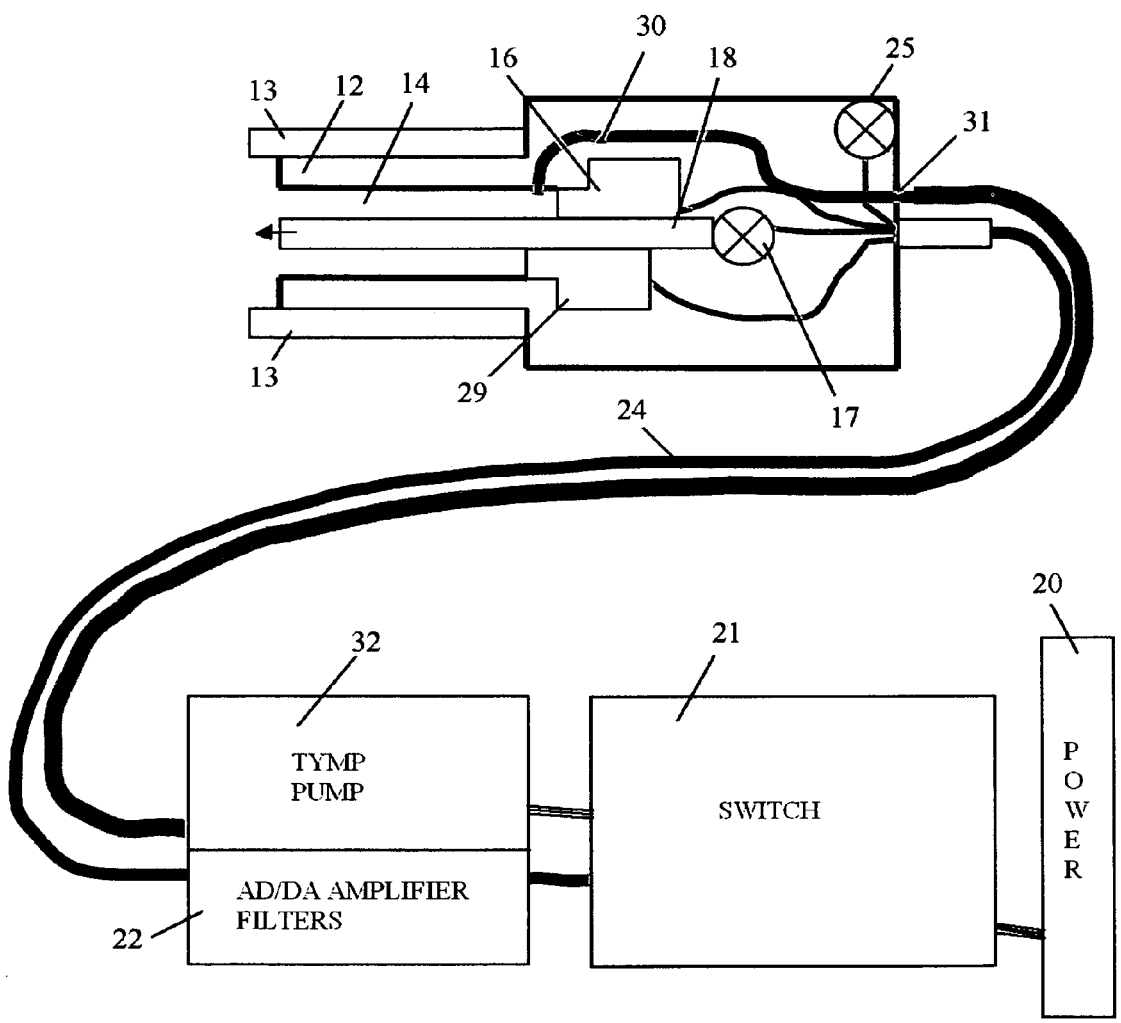
FIG. 4 is a cross-section view of another preferred embodiment used for Timpanometrie.

FIG. 4 is a cross-section view of another preferred embodiment used for Timpanometrie. In addition to the probe 10 components described above, a microphone(s) and/or pressure sensor 29 is included and positioned within the housing 11 to sense pressure and audio responses transmitted through the passageway 14.

In communication with the passageway 14 of the housing 11 is a tymp air tube 30 to adjust the pressure within the passageway 14 and inner ear canal. The tymp air tube 30 is secured to the housing 11 with a tymp tube connector 31. The tymp air tube 30 is operatively associated with a tymp pump 32, which increases the pressure within the tymp air tube 30, which in turn increases the pressure within the passageway 14 and inner ear canal. The tymp pump 32 is controlled by the microprocessor 21. As the tymp pump 32 varies the pressure within the ear canal, response signals are received by the microphone(s) and/or pressure sensor 29 and transmitted to the microprocessor 21 for analysis and subsequent recording or display.

FIG. 4 thus provides an ear canal obstruction detecting acoustical stimulation ear probe 10 including a tymp air tube 30 for applying static air pressure to the ear, thus allowing tympanometry testing.

Although this specification has made reference to the illustrated embodiments, it is not intended to restrict the scope of the claims. The claims themselves recite those features deemed essential to the invention.

We claim:

1. An ear canal obstruction detecting acoustical stimulation ear probe comprising:
   a. a housing with
      i. an exterior sized for hand positioning the probe, and
      ii. a tip with a tip exterior defining a tip opening light passageway, the tip exterior structured to fit and seal within the ear canal to align the tip opening in communication with an ear canal, when inserted,
   b. a light mounted within the housing structured to radiate energy through the tip opening light passageway into the ear canal to illuminate the outer ear canal to identify wax or other debris for removal before sound testing and to aid in probe placement,
   c. at least one acoustical transducer, which sends sound signals and receives otoacoustical and/or obstruction reflection signals, mounted to the housing with leads extending from the housing,
   d. a power source operably associated with the leads of the acoustical transducers to activate at least one of the acoustical transducers to send sound signals and receive otoacoustical and/or obstruction reflection signals, and
   e. a microprocessor associated with the acoustical transducers to process the signals for display.

2. An ear canal obstruction detecting acoustical stimulation ear probe according to claim 1, including:
   a. a sensor associated with the housing, which generates a signal to the microprocessor when the housing tip is property seated within the outer ear channel of a test subject, and
   b. an indicator attached to the exterior of the housing and associated with the microprocessor, which activates the indicator when sensor signals indicate the housing tip is properly seated within the outer ear channel of the test subject.

3. An ear canal obstruction detecting acoustical stimulation ear probe according to claim 2, wherein the sensor is a pressure sensor associated with a source of gas to increase pressure within the ear canal to detect if the housing tip seal leaks.

4. An ear canal obstruction detecting acoustical stimulation ear probe according to claim 2, wherein the sensor is a sound sensor to detect if the housing tip seal is leaking energy from the acoustical transducer.

5. An ear canal obstruction detecting acoustical stimulation ear probe according to claim 2, wherein the sensor is a contact sensor to detect if the housing tip contacts walls of the ear canal to form a seal.

6. An ear canal obstruction detecting acoustical stimulation ear probe according to claim 2, wherein the indicator also signals test progress, probe placement quality parameters, and environmental noise.

7. An ear canal obstruction detecting acoustical stimulation ear probe according to claim 6, wherein the indicator indicates the end of a test and its results.

8. An ear canal obstruction detecting acoustical stimulation ear probe according to claim 1, wherein the acoustical transducer includes at least one speaker and at least one microphone, which can he used to evoke and record otoacoustic emissions and obstruction reflection signals.

9. An ear canal obstruction detecting acoustical stimulation ear probe according to claim 1, including a tube connection for applying static air pressure to the ear, thus allowing tympanometry testing.

10. An ear canal obstruction detecting acoustical stimulation ear probe according to claim 1, wherein the transducer and microprocessor are configured to optimize measuring acoustic impedance of the ear canal.

11. An ear canal obstruction detecting acoustical stimulation ear probe according to claim 1, including a switch for turning on and off a light source and frequency emitter.

12. An ear canal obstruction detecting acoustical stimulation ear probe according to claim 1, wherein the light is an LED.

13. An ear canal obstruction detecting acoustical stimulation ear probe according to claim 1, including a magnifier lens placed within the housing passageway for magnifying views of the ear canal for inspection.

14. An ear canal obstruction detecting acoustical stimulation ear probe according to claim 1, including a camera placed within the housing passageway for ear canal inspection.

15. An ear canal obstruction detecting acoustical stimulation ear probe according to claim 1, including an indicator light attached to the housing and operatively associated with the microprocessor, which changes colors when the probe is properly seated.

16. An ear canal obstruction detecting acoustical stimulation ear probe comprising:
 a. a housing with
  i. an exterior sized for hand positioning the probe,
  ii. a tip with exterior defining a tip opening, the tip exterior structured to fit and seal within the ear canal to align the tip opening in communication with an ear canal, when inserted, and
  iii. an interior defining a light transmission and inspection passageway in communication with the tip opening,
 b. an acoustical transducer, which sends sound signals and receives otoacoustical signals mounted within the housing passageway with leads extending from the housing,
 c. a power source operably associated with the leads of the acoustical transducer to activate the acoustical stimulator to send sound signals and receive otoacoustical signals,
 d. a microprocessor associated with the acoustical transducer to process the otoacoustical signals,
 e. a frequency emitter associated with the housing passageway to radiate energy from the passageway into the ear canal to identify wax or other debris for removal before sound testing,
 f. a sensor associated with the housing tip, which generates an ongoing sensor signal to the microprocessor when the housing tip is properly seated within the outer ear channel of a test subject,
 g. an indicator attached to the exterior of the housing and associated with the microprocessor, which activates the indicator when the sensor signal indicates the housing tip is properly seated within the outer ear channel of the test subject, and
 h. a light mounted within the housing passageway and powered by the power source to transmit light through the light transmission and inspection passageway through the tip opening to illuminate the outer ear to expose wax and debris while the probe is being placed.

17. An ear canal obstruction detecting acoustical stimulation ear probe according to claim 16, wherein the housing is tubular with an open viewing end leading into the passageway, and including a magnifier lens mounted within the passageway for increased magnification ear canal inspection.

18. An ear canal obstruction detecting acoustical stimulation ear probe according to claim 16, including a camera mounted within the passageway positioned to view the ear canal through the opening of the tip for ear canal inspection.

19. An ear canal obstruction detecting acoustical stimulation ear probe according to claim 16, including interchangeable ear tips associated with the housing structured to fit and seal within an ear canal.

\* \* \* \* \*